United States Patent
Sun et al.

(10) Patent No.: US 11,123,033 B2
(45) Date of Patent: Sep. 21, 2021

(54) MOLECULAR IMAGING METHOD FOR EVALUATING LIVER REGENERATION CAPACITY AFTER ALPPS OPERATION

(71) Applicant: Harbin Medical University, Harbin (CN)

(72) Inventors: Xilin Sun, Harbin (CN); Zhen Quan, Harbin (CN); Ruifeng Wang, Harbin (CN); Kai Wang, Harbin (CN); Lili Yang, Harbin (CN); Zunyu Xiao, Harbin (CN); Yang Liu, Harbin (CN); Zhaoguo Han, Harbin (CN); Xiang Liu, Harbin (CN); Mingxing Ke, Harbin (CN)

(73) Assignee: Harbin Medical University, Harbin (CN)

( * ) Notice: Subject to any disclaimer, the term of this patent is extended or adjusted under 35 U.S.C. 154(b) by 0 days.

(21) Appl. No.: 17/039,984

(22) Filed: Sep. 30, 2020

(65) Prior Publication Data

US 2021/0015439 A1    Jan. 21, 2021

(30) Foreign Application Priority Data

Jul. 30, 2019   (CN) .......................... 201910696894.5

(51) Int. Cl.
*A61B 6/03* (2006.01)
*A61B 6/00* (2006.01)
(Continued)

(52) U.S. Cl.
CPC .............. *A61B 6/508* (2013.01); *A61B 6/027* (2013.01); *A61B 6/032* (2013.01); *A61B 6/037* (2013.01);
(Continued)

(58) Field of Classification Search
CPC ......... A61B 6/508; A61B 6/027; A61B 6/032; A61B 6/037; A61B 6/5235; A61K 51/04;
(Continued)

(56) References Cited

PUBLICATIONS

Sun et al., "Underlying Pathophysiological Mechanism of ALPPS in Rabbit VX2 Liver Tumors Model: Molecular and functional Imaging Findings" Journal of Nuclear Medicine May 2019 (supplement 1) 1413 (Year: 2019).*

(Continued)

*Primary Examiner* — Colin T. Sakamoto

(57) ABSTRACT

Disclosed is a molecular imaging method for evaluating liver regeneration ability after ALPPS. The method includes steps of: 1) preparing a VX2 rabbit liver cancer model; 2) performing ALPPS for the VX2 rabbit liver cancer model; 3) synthesizing 18F-Fluoromethylcholine (18F-Methylcholine, 18F-FCH); 4) PET/CT imaging and data processing for $^{18}$F-FCH. The disclosure is the first to propose the use of 18F-FCH PET/CT to monitor the proliferative capacity of residual liver, and further indirectly reflect the increased ability of cell membrane synthesis on the basis that 18F-FCH has higher choline metabolism in residual liver tissue, so that the liver regeneration ability after ALPPS is evaluated by the molecular imaging method, thereby providing important new ideas for the clinical selection of ALPPS to choose the best time for second-stage surgery.

1 Claim, 3 Drawing Sheets

(51) Int. Cl.
*A61B 6/02* (2006.01)
*A61K 51/04* (2006.01)
*A61B 17/00* (2006.01)

(52) U.S. Cl.
CPC ............ *A61B 6/5235* (2013.01); *A61K 51/04* (2013.01); *A01K 2207/12* (2013.01); *A01K 2227/107* (2013.01); *A01K 2267/0331* (2013.01); *A61B 2017/00778* (2013.01)

(58) Field of Classification Search
CPC .......... A61K 2207/12; A61K 2227/107; A61K 2267/0331
See application file for complete search history.

(56) References Cited

PUBLICATIONS

Rodnick et al., "A fully-automated one-pot synthesis of [18F]fluoromethylcholine with reduced dimethylaminoethanol contamination via [18F]fluoromethyl tosylate" Applied Radiation and Isoopes vol. 78, Aug. 2013, p. 26-32 (Year: 2013).*

Parvinian et al., "Development, growth, propagation, and angiographic utilization of the rabbit VX2 model of liver cancer: a pictorial primer and "how to" guide". Diagnostic and Interventional Radiology vol. 20, issue 4, pp. 335-340, Jul. 2014 (Year: 2014).*

Popescu et al., "Good To Know: The ALPPS Procedure— Embracing a New Technique". Chirurgia (Bucur). May-Jun. 2017;112(3):332-341 (Year: 2017).*

* cited by examiner

MOLECULAR IMAGING METHOD FOR EVALUATING LIVER REGENERATION CAPACITY AFTER ALPPS OPERATION

CROSS REFERENCE TO RELATED APPLICATION

This application claims priority of Chinese Application No. CN 2019106968945 filed on 2019 Jul. 30 and entitled "molecular imaging method for evaluating liver regeneration capacity after ALPPS operation".

FIELD OF TECHNOLOGY

The disclosure relates to the medical field, in particular, to a molecular imaging method for evaluating liver regeneration ability after ALPPS.

BACKGROUND

In the prior art, associating liverpartition and portal vein ligation for staged hepatectomy (ALPPS) is an emerging surgical method for liver malignant tumors. By inducing rapid proliferation of residual liver tissue (FLR), it effectively reduces liver failure caused by insufficient residual liver volume after liver cancer resection, thereby increasing the chance of radical resection. The regeneration ability and function of residual liver after first-stage ALPPS surgery is particularly important for choosing the best second-stage surgery time. Previous clinical studies used traditional imaging techniques such as CT or MRI to measure the residual liver volume after surgery, and indirectly predict the postoperative liver function of patients to guide the clinically further second-phase resection. Although traditional imaging methods can measure the residual liver volume, the residual liver volume is not completely equal to liver function, which has great limitations for improving the prognosis of patients with ALPPS. Serological methods for detecting liver function often fail to reflect changes in liver function in a timely manner and have a large error. Therefore, the real-time, dynamic, and accurate monitoring and evaluation for the regeneration ability of the residual liver after the first-stage of ALPPS is a difficult problem that requires a new method to solve. The molecular imaging technology can monitor the response of tumors or organs to treatment by evaluating functional information such as proliferation and metabolism. Through 18 F-methylcholine (18 F-FCH) PET/CT imaging, the disclosure mainly indirectly reflects liver regeneration ability by reflecting the phospholipid synthesis of the liver cell membrane. The molecular imaging is very promising in studying pathological and physiological changes after ALPPS.

SUMMARY

In view of the existing shortcomings in evaluating the residual liver volume and function after ALPPS, an object of the disclosure realizes real-time, dynamic and accurate monitoring and evaluation of the regeneration ability of residual liver after first-stage of ALPPS through PET imaging technology, so as to provide a more scientific and reasonable basis for the clinical guidance of the second-stage surgery.

The technical solution of the disclosure is as below: a molecular imaging method for evaluating liver regeneration ability after ALPPS, including steps of:

step one, preparing a VX2 rabbit liver cancer model, including:

first inoculating a VX2 tumor strain into the muscle outside the rabbit hind leg after passage, wherein the tumor grows to a diameter of 2.0-3.0 cm after 3 weeks; removing the tumor in the muscle of the rabbit hind, eliminating the necrotic tissue, selecting fish-like tissue at the edge of the tumor, and using ophthalmic scissors to cut the tumor tissue into tissue blocks of 1 mm3, and washing repeatedly with saline and putting in a sterile Petri dish for use; putting an experimental rabbit into general anesthesia and fixing it on an animal operating table in supine position; performing skin preparation, disinfection, and spreading sterile surgical scarves on a surgical region of a rabbit abdomen; injecting lidocaine into linea alba 1 cm below xiphoid process for local anesthesia, and making a midline incision in an upper abdomen and cutting abdominal wall layer by layer to expose a left lateral lobe of a liver; cutting a thicker liver lobe to form a hole passage of about 3 mm×3 mm, and implanting 3-5 tumors into it, then filling liver incision with gelatin sponge particles and pressing to stop bleeding, followed by suturing the incision and closing the abdomen;

step two, performing ALPPS on the rabbit VX2 liver cancer model, including:

two weeks after implanting the rabbit liver with the VX2 tumor strain, performing the first stage of ALPPS on tumor-bearing rabbits;

dividing the tumor-bearing rabbits randomly into an ALPPS group and a Sham group; fasting rabbits in the ALPPS group for 12 hours before surgery, and fixing on the table in the supine position after general anesthesia, and performing skin preparation in the surgical region; injecting lidocaine into the left under the xiphoid process, opening the abdomen after anesthesia around the incision with an incision length of 5-7 cm, exposing and separating the left branch of the portal vein and ligating with 4-0 surgical sutures, then after an ischemic line between the left and right liver is formed, using the surgical scissors to cut off the liver parenchyma along the ischemic line; performing hemostasis, suturing the abdominal wall incision, closing abdominal cavity, and disinfecting;

step three, synthesizing 18F-FCH, including:

fully automatically synthesizing with GE Tracerlab FX-FN module, specifically including steps of:

(1) producing [18F] by a cyclotron PETtrace through the 18O (p, n) 18F reaction;

(2) delivering [18F] fluoride from the cyclotron and capturing in QMA-Light Sep-Pak to remove [18O] H2O;

(3) then using K2CO3 solution for [18F], and eluting fluoride into a reaction vessel;

(4) adding the solution of kryptofix 2.2.2 to the reaction vessel, and heating to 80° C. and evacuating for 4 minutes;

(5) cooling the reaction vessel to 60±1° C. while performing helium flow, vacuum adsorption for 4 minutes;

(6) adding a solution of 7-8 mg of dimethylxylene sulfonic acid in anhydrous acetonitrile and sterile water to dry [18 F] fluoride, and heating the reactants to 120° C. while stirring for 10 minutes, then cooling the reaction mixtures to 50° C.;

(7) then adding choline precursor DMAE, heating it to 120° C. and stirring for 10 minutes;

(8) then cooling the reaction mixtures to 60° C., and performing evaporation of the reaction solvent by maintaining 60° C., and continuously performing the reaction with helium gas flow and vacuum suction for 5 minutes;

(9) adding sterile water to the dried reactants, entering into a round bottom flask containing ethanol through C18-

Plus Sep-Pak to capture unreacted ditosylmethane and [18 F] fluoromethyl tosylate as well as any tosylmethylcholine produced as a by-product;

(10) transferring a water/ethanol mixture through CM-Light Sep-Pak to the desired [18 F] fluoromethylcholine;

(11) washing CM-Light Sep-Pak with ethanol to remove unreacted DMAE and water to remove residual ethanol to waste;

(12) subsequently, eluting [18 F] fluoromethylcholine to contain 0.9% saline for injection;

(13) then, introducing final preparation into a sterile dose vial through a 0.22 mm sterile filter to provide 18F-FCH as an isotonic solution to obtain the product, wherein the product 18F-FCH has a radiochemical purity greater than 90%, and a specific activity of >30 GBq/pmol, which may be used for PET imaging.

step four, PET/CT imaging and data processing for 18 F-FCH, including:

performing 18F-FCH PET/CT scan on the tumor-bearing rabbits in the ALPPS group and the Sham group at 0 d before surgery, 1 d, 3 d, 7 d, and 14 d after surgery;

1) fasting the rabbits for more than 6 hours, with general anesthesia;

2) injecting each group of the tumor-bearing rabbits with 37 MBq/kg (1 mci/kg) 18F-FCH through the otogenic vein;

3) performing PET/CT scan 1 h after injection of 18F-FCH; fixing the experimental rabbits on a scanning bed in the supine position, first performing low-dose spiral CT axial scanning, and then performing PET emission scanning; using low-dose CT for attenuation correction and iterative reconstruction to obtain PET images, transferring the image data to a GE AW4.6 PET post-processing workstation to obtain CT, PET and PET/CT fusion images of the experimental rabbits, wherein CT scan parameters are a voltage of 120 KV, a current of 10 mA and a layer thickness of 3.33 mm, and PET acquisition method is 3D mode, with 1 scanning bed and 3 min per bed;

4) outlining interest regions of the residual liver to obtain a maximum standardized uptake value and a mean standardized uptake value in the rabbit 18F-FCH PET/CT images, and outlining a three-dimensional structure of the liver and measuring the functional volume of the liver through the GE AW4.6 workstation.

The disclosure has the following advantages:

1. In the disclosure, the molecular imaging technology is used for the first time to evaluate the changes of residual liver morphology and function after the first-stage of ALPPS on the liver cancer, reveal the regeneration ability of liver, and further guide clinically to choose the best time for second-stage surgery.

2. In the past, the optimal time for ALPPS surgery was chosen clinically, mainly by measuring liver volume through routine imaging examination or detecting liver function by serological examination, but the method has many limitations. The disclosure uses 18 F-FCH PET/CT imaging and data processing technology to visualize the process of liver regeneration, and real-time and dynamic monitoring of liver volume and function changes.

3. In the past, 18 F-FCH was mainly used to diagnose cancer. In the disclosure, 18 F-FCH is used to evaluate the regeneration ability of liver, which is the first application of the molecular probe to evaluate tissue regeneration.

4. The disclosure proposes a new concept called Valid Volumetric Function (WF) to reflect the real function of residual liver, which is equivalent to FLRSUV mean×FLRV FCH). This indicator may combine the function and volume of the liver as a technical indicator reflecting the true regeneration capacity of the liver.

The disclosure will be further described in combination with drawings and embodiments.

DETAILED DESCRIPTION

Figure 1:
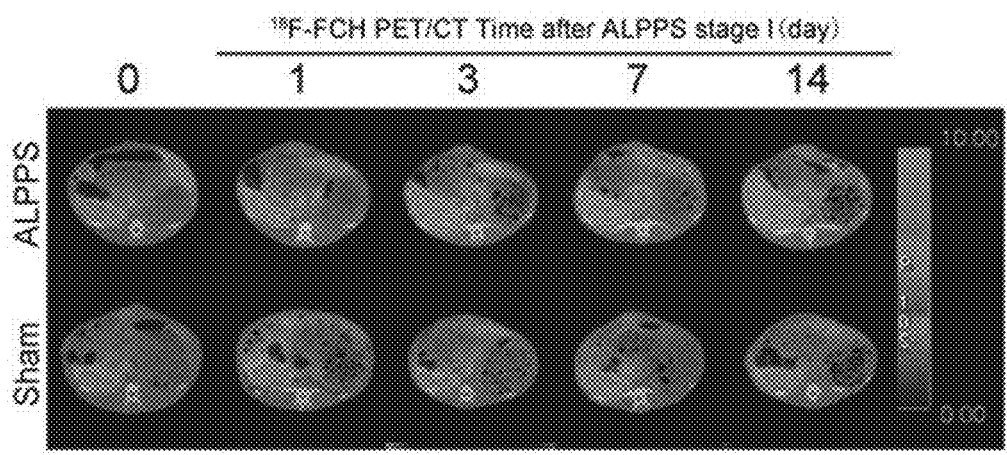
FIG. 1: 18 F-FCH PET/CT imaging (from horizontal axis) of rabbit VX2 liver cancer model.
Figure 2:
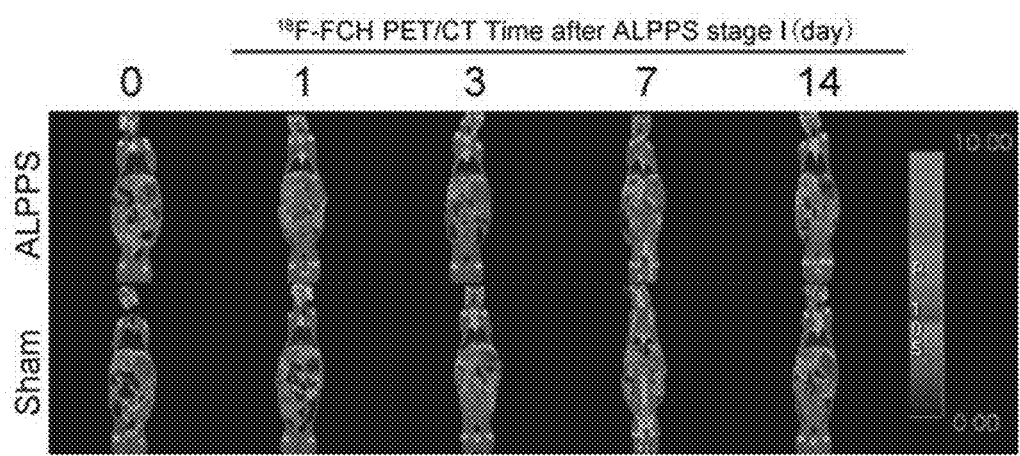
FIG. 2: 18 F-FCH PET/CT imaging (from coronal position) of rabbit VX2 liver cancer model.
Figure 3:
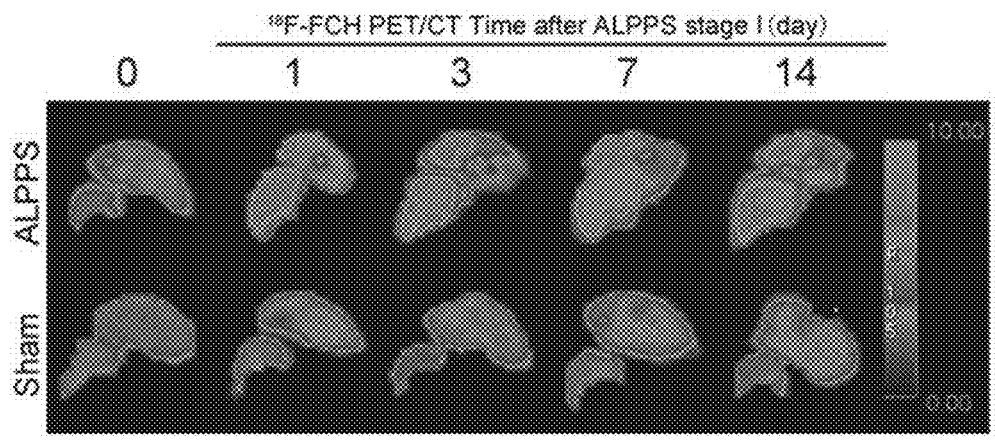
FIG. 3: Visible Changes of 18 F-FCH uptake and changes of liver morphology in ALPPS group after three-dimensional reconstruction of liver through PET post-processing technology.

A molecular imaging method for evaluating liver regeneration ability after ALPPS:

step one, preparing a VX2 rabbit liver cancer model, including:

using incision and fragmentation method for liver cancer tissues; first inoculating a VX2 tumor strain into the muscle outside the rabbit hind leg after passage, wherein the tumor grows to a diameter of 2.0-3.0 cm after 3 weeks; removing the tumor in the muscle of the rabbit hind, eliminating the necrotic tissue, selecting fish-like tissue at the edge of the tumor, and using ophthalmic scissors to cut the tumor tissue into tissue blocks of 1 mm3, and washing repeatedly with saline and putting in a sterile Petri dish for use; putting an experimental rabbit into general anesthesia (method of anesthesia: intramuscular injection of Shutai 1 ml) and fixing it on an animal operating table in supine position; performing skin preparation, disinfection, and spreading sterile surgical scarves on a surgical region of a rabbit abdomen; injecting lidocaine into linea alba 1 cm below xiphoid process for local anesthesia, and making a midline incision of 4 to 5 cm in an upper abdomen and cutting abdominal wall layer by layer to expose a left lateral lobe of a liver; cutting a thicker liver lobe to form a hole passage of about 3 mm×3 mm, and implanting 3-5 tumors into it, then filling liver incision with gelatin sponge particles and pressing to stop bleeding, followed by suturing the incision and closing the abdomen.

step two, performing ALPPS on the rabbit VX2 liver cancer model, including:

two weeks after implanting the rabbit liver with the VX2 tumor strain, performing the first stage of ALPPS (i.e. associating liverpartition and portal vein ligation for staged hepatectomy) on tumor-bearing rabbits;

dividing the tumor-bearing rabbits randomly into an ALPPS group (the left branch of the portal vein of the liver is ligated, and the liver parenchyma is dissected along the ischemic line between the left middle lobe of the liver and the right lobe of the liver) and a Sham group (i.e., a sham operation group, no portal vein ligation and liver dissection); fasting rabbits in the ALPPS group for 12 hours before surgery, and fixing on the table in the supine position after general anesthesia, and performing skin preparation in the surgical region; injecting lidocaine into the left under the xiphoid process, opening the abdomen after anesthesia around the incision with an incision length of about 5-7 cm, exposing and separating the left branch of the portal vein and ligating with 4-0 surgical sutures, then after an ischemic line between the left and right liver is formed, using the surgical scissors to cut off the liver parenchyma along the ischemic line; filling the partition with gel sponge particles for hemostasis, after no obvious bleeding, closing the abdominal wall incision layer by layer, closing the abdominal cavity, and disinfecting the incision with iodophor.

step three, synthesizing 18F-FCH, including:
fully automatically synthesizing with GE Tracerlab FX-FN module, specifically including steps of:

(1) producing [18F] by a cyclotron PETtrace through the 18O (p, n) 18F reaction;

(2) delivering [18F] fluoride from the cyclotron and capturing in QMA-Light Sep-Pak to remove [18O] H2O;

(3) then using K2CO3 solution (3.0 mg, in water of 0.5 mL) for [18F], and eluting fluoride into a reaction vessel;

(4) adding the solution of kryptofix 2.2.2 (15 mg, in acetonitrile of 1 mL) to the reaction vessel; heating the reaction vessel to 80° C. and evacuating for 4 minutes;

(5) cooling the reaction vessel to 60±1° C. while performing helium flow, vacuum adsorption for 4 minutes;

(6) adding a solution of 7-8 mg of dimethylxylene sulfonic acid in anhydrous acetonitrile (10 µl) and sterile water to dry [18 F] fluoride, and heating the reactants to 120° C. while stirring for 10 minutes; then cooling the reaction mixtures to 50° C.;

(7) then adding choline precursor DMAE (40 µl, in MeCN of 350 µl), heating it to 120° C. and stirring for 10 minutes;

(8) then cooling the reaction mixtures to 60° C., and performing evaporation of the reaction solvent by maintaining 60° C., and continuously performing the reaction with helium gas flow and vacuum suction for 5 minutes;

(9) adding sterile water (11 mL) to the dried reactants, entering into a round bottom flask containing ethanol (10 mL) through C18-Plus Sep-Pak to capture unreacted ditosylmethane and [18 F] fluoromethyl tosylate as well as any tosylmethylcholine produced as a by-product;

(10) transferring a water/ethanol mixture through CM-Light Sep-Pak to the desired [18 F] fluoromethylcholine;

(11) washing CM-Light Sep-Pak with ethanol (15 mL) to remove unreacted DMAE and water (20 mL) to remove residual ethanol to waste;

(12) subsequently, eluting [18 F] fluoromethylcholine to contain 0.9% saline for injection (10 mL);

(13) then, introducing final preparation (10 mL) into a sterile dose vial through a 0.22 mm sterile filter to provide 18F-FCH as an isotonic solution to obtain the product, wherein the product 18F-FCH has a radiochemical purity greater than 90%, and a specific activity of >30 GBq/µmol, which may be used for PET imaging.

step four, PET/CT imaging and data processing for 18 F-FCH, including:
performing 18F-FCH PET/CT scan on the tumor-bearing rabbits in the ALPPS group and the Sham group at 0 d before surgery, 1 d, 3 d, 7 d, and 14 d after surgery;

1) fasting the rabbits for more than 6 hours, and performing intramuscular injection of Shutai 1 ml for general anesthesia;

2) injecting each group of the tumor-bearing rabbits with 37 MBq/kg (1 mci/kg) 18F-FCH through the otogenic vein;

3) performing PET/CT scan 1 h after injection of 18F-FCH; fixing the experimental rabbits on a scanning bed in the supine position, first performing low-dose spiral CT axial scanning, and then performing PET emission scanning; using low-dose CT for attenuation correction and iterative reconstruction to obtain PET images, transferring the image data to a GE AW4.6 PET post-processing workstation to obtain CT, PET and PET/CT fusion images of the experimental rabbits, wherein CT scan parameters are a voltage of 120 KV, a current of 10 mA and a layer thickness of 3.33 mm, and PET acquisition method is 3D mode, with 1 scanning bed and 3 min per bed;

4) outlining regions of interest of the residual liver to obtain a maximum standardized uptake value (SUVmax) and an mean standardized uptake value in the rabbit 18F-FCH PET/CT images; and outlining a three-dimensional structure of the liver and measuring the functional volume of the liver through the GE AW4.6 workstation (on the basis of >42% SUVmax).

Figure 4:
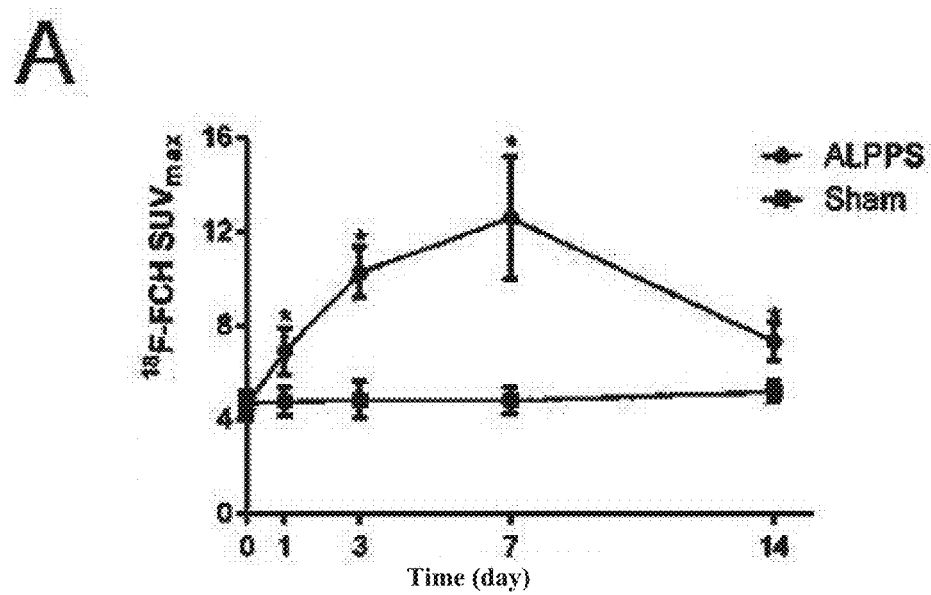
FIG. 4: A, comparison between 18 F-FCH SUV max in the residual liver of ALPPS group and sham group.
Figure 5:
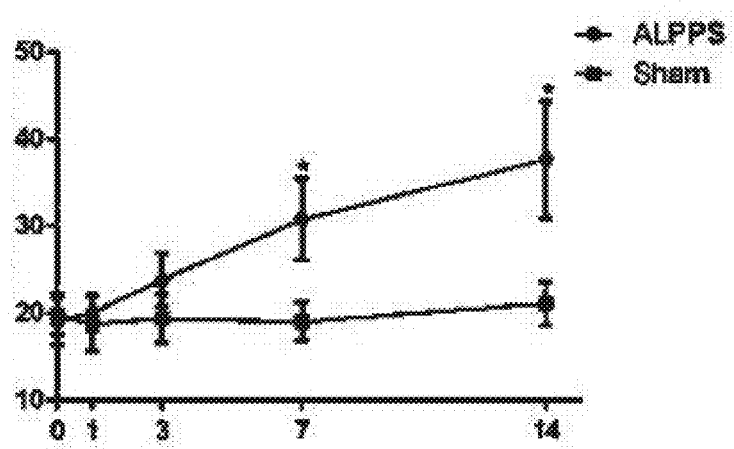
FIG. 5: B, changes in liver functional volume at various time points after surgery.
Figure 6:
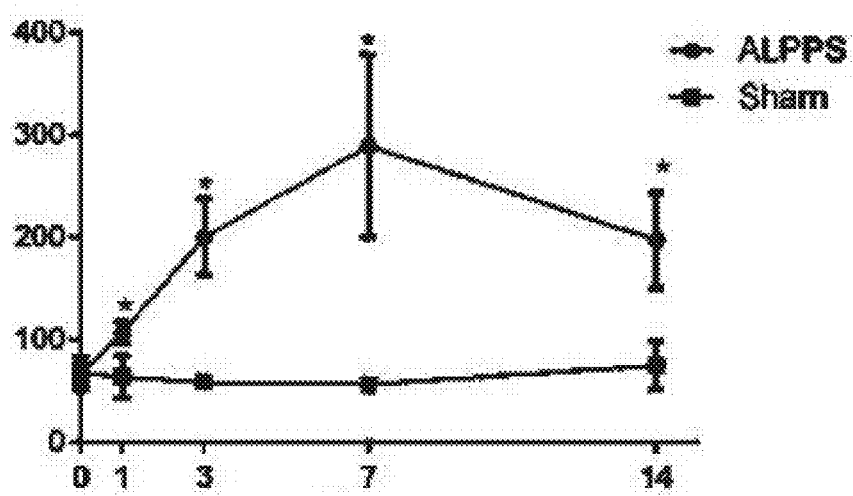
FIG. 6: C, changes in valid volumetric function at various time points after surgery.

Results from Data Processing:

In the first-stage of ALPPS surgical model for the liver cancer, 18 F-FCH in the residual liver tissue of the ALPPS group shows significant high uptake from the 1st postoperative day, indicating that choline metabolism is enhanced and hepatocyte proliferation is active, which is consistent with the rapid increase in residual liver volume caused by ALPPS surgery. In the first 3 days after surgery, 18 F-FCH uptake increases rapidly and reaches a peak around 7 days, indicating that the proliferation of liver cells is most active around 7 d, and that the regeneration capacity of liver is the strongest at this time; 18 F-FCH intake decreases slightly after 14 days, indicating that the regeneration capacity of liver begins to decrease. Meanwhile, through PET imaging technology, we may reconstruct a three-dimensional structure of the liver, and then see the real functional changes of the liver in real time, dynamically and intuitively. Although 18 F-FCH uptake decreases in the liver after 7 days, the volume is still increasing. At this time, the volume may no longer reflect the real function of the liver. We defines a new concept called Valid Volumetric Function (VVF) to reflect the real function of residual liver, which is equivalent to FLRSUV meanxFLRV FCH. In our disclosure, we have successfully found that VVF increases significantly from 3 d, and reaches a highest value at 7 d, indicating that the liver has the strongest regeneration ability at this time, and that the best time for clinically choosing second-stage surgery may be 3-7 days after first-stage surgery (see FIGS. 1, 2, 3, 4, 5, 6; in FIG. 4, A residual liver 18 F-FCH SUV max; in FIG. 5, B functional volume of residual liver; in FIG. 6, C valid volumetric function of residual liver.* Compared with the Sham group, for the ALPPS group, P<0.05).

The disclosure is the first to propose the use of 18 F-FCH PET/CT to monitor the proliferative capacity of residual liver, and further indirectly reflect the increased ability of cell membrane synthesis on the basis that 18F-FCH has higher choline metabolism in residual liver tissue, so that the liver regeneration ability after ALPPS is evaluated by the molecular imaging method. Although these results are currently in pre-clinical studies, the time window of the second-stage surgery of ALPPS in humans may be different, but it provides important new ideas for the clinical selection of the best time for ALPPS to choose the second-stage surgery.

What is claimed is:

1. A molecular imaging method for evaluating liver regeneration capacity after an associating liver partition and portal vein ligation for staged hepatectomy (ALPPS) operation, the method comprising:
    (1) preparing a plurality of VX2 rabbit liver cancer models, wherein the plurality of VX2 rabbit liver cancer models are divided into two groups of rabbits: an ALPPS group and a Sham group;

(2) performing ALPPS on the rabbits in the ALPPS group two weeks after step (1);
(3) synthesizing $^{18}$F-fluorocholine ($^{18}$F-FCH) with a radiotracer synthesizer;
(4) performing $^{18}$F-FCH Positron Emission Tomography (PET)/Computed Tomography (CT) scans on the rabbits of the ALPPS group and the rabbits of the Sham group at 0 days before step (2), and 1 day, 3 days, 7 days, and 14 days after step (2), wherein each $^{18}$F-FCH PET/CT scan of each respective rabbit of the ALPPS group and the Sham group comprises:
  (4.1) preparing the respective rabbit for PET/CT scanning by performing the following:
    (4.1.1) having the respective rabbit fast for more than 6 hours, and applying general anesthesia;
    (4.1.2) injecting the respective rabbit with 37 MBq/kg (1 mci/kg) of the synthesized $^{18}$F-FCH through an otogenic vein;
    (4.1.3) fixing the respective rabbit on a scanning bed in a supine position,
  (4.2) performing a PET/CT scan 1 hour after the injection of the $^{18}$F-FCH by performing the following:
    (4.2.1) first performing a low-dose spiral CT axial scan of the respective rabbit to acquire CT imaging data, wherein the low-dose spiral CT axial scan is performed using the following CT scan parameters: a voltage of 120 kV, a current of 10 mA, and a layer thickness of 3.33 mm; and
    (4.2.2) then performing a PET scan of the respective rabbit to acquire PET imaging data, wherein the PET scan is performed in a 3D mode, with 1 scanning bed at 3 minutes per bed; and
    (4.2.3) transferring the CT imaging data and the PET imaging data to a post-processing workstation;
(5) using the post-processing workstation to obtain $^{18}$F-FCH PET/CT images from the CT imaging data and the PET imaging data, wherein the $^{18}$F-FCH PET/CT images comprise CT images, PET images, and PET/CT fusion images of each rabbit, wherein the post-processing workstation iteratively reconstructs the PET images from the PET imaging data using attenuation correction based on the CT images; and
(6) performing the following image analyses with the post-processing workstation:
  (6.1) outlining interest regions of a residual liver in the $^{18}$F-FCH PET/CT images to obtain a maximum standardized $^{18}$F-FCH uptake value and a mean standardized $^{18}$F-FCH uptake value, and
  (6.2) outlining a three-dimensional structure of the residual liver and measuring a functional volume of the residual liver.

\* \* \* \* \*